United States Patent [19]
Samson

[11] Patent Number: 5,927,345
[45] Date of Patent: Jul. 27, 1999

[54] SUPER-ELASTIC ALLOY BRAID STRUCTURE

[75] Inventor: Gene Samson, Milpitas, Calif.

[73] Assignee: Target Therapeutics, Inc., Fremont, Calif.

[21] Appl. No.: 08/640,342

[22] Filed: Apr. 30, 1996

[51] Int. Cl.[6] .................................................. F16L 11/02
[52] U.S. Cl. ...................... 138/127; 138/123; 138/153; 138/172
[58] Field of Search .................................. 138/123, 124, 138/127, 153, 172

[56] References Cited

U.S. PATENT DOCUMENTS

| | | | |
|---|---|---|---|
| 2,367,944 | 1/1945 | Ingalls ........................ | 138/124 |
| 2,437,542 | 3/1948 | Krippendorf . | |
| 2,761,203 | 9/1956 | De Witt, Sr. ................ | 138/124 |
| 3,174,851 | 3/1965 | Buehler et al. . | |
| 3,351,463 | 11/1967 | Rozner et al. . | |
| 3,416,531 | 12/1968 | Edwards . | |
| 3,725,192 | 4/1973 | Satoshi et al. ............... | 138/141 |
| 3,753,700 | 8/1973 | Harrison et al. . | |
| 3,924,632 | 12/1975 | Cook . | |
| 3,997,638 | 12/1976 | Manning et al. ............. | 264/29.7 |
| 4,329,157 | 5/1982 | Dobo et al. .................. | 55/16 |
| 4,348,458 | 9/1982 | Otstot ........................... | 428/366 |
| 4,425,919 | 1/1984 | Alston, Jr. et al. . | |
| 4,484,586 | 11/1984 | McMickle et al. . | |
| 4,516,972 | 5/1985 | Samson . | |
| 4,569,382 | 2/1986 | Maxey et al. ................ | 152/548 |
| 4,806,182 | 2/1989 | Rydell et al. . | |
| 4,832,681 | 5/1989 | Lenck . | |
| 4,981,478 | 1/1991 | Evard et al. . | |
| 5,037,404 | 8/1991 | Gold et al. . | |
| 5,057,092 | 10/1991 | Webster, Jr. . | |
| 5,176,660 | 1/1993 | Truckai . | |
| 5,236,013 | 8/1993 | Das ............................... | 137/592 |
| 5,248,305 | 9/1993 | Zdrahala . | |
| 5,273,080 | 12/1993 | Morohashi et al. ......... | 138/124 |
| 5,437,282 | 8/1995 | Koger et al. . | |
| 5,501,694 | 3/1996 | Ressemann et al. . | |
| 5,551,484 | 9/1996 | Charboneau ................. | 138/104 |
| 5,562,126 | 10/1996 | Briand et al. ................ | 138/123 |

FOREIGN PATENT DOCUMENTS

| | | |
|---|---|---|
| 05-220225 | 8/1993 | Japan . |
| 1422936 | 1/1976 | United Kingdom . |

*Primary Examiner*—Denise L. Ferensic
*Assistant Examiner*—James F. Hook
*Attorney, Agent, or Firm*—Morrison & Foerster LLP

[57] ABSTRACT

This is a braided tubular structure made up of a plurality of interwoven fibrous members, preferably ribbons, a majority of which comprise one or more superelastic and (at least) ternary alloys of nickel, titanium, and at least about 1.5% (wt) of one or more alloying members selected from the group consisting of vanadium, chromium, manganese, iron, and cobalt.

16 Claims, 2 Drawing Sheets

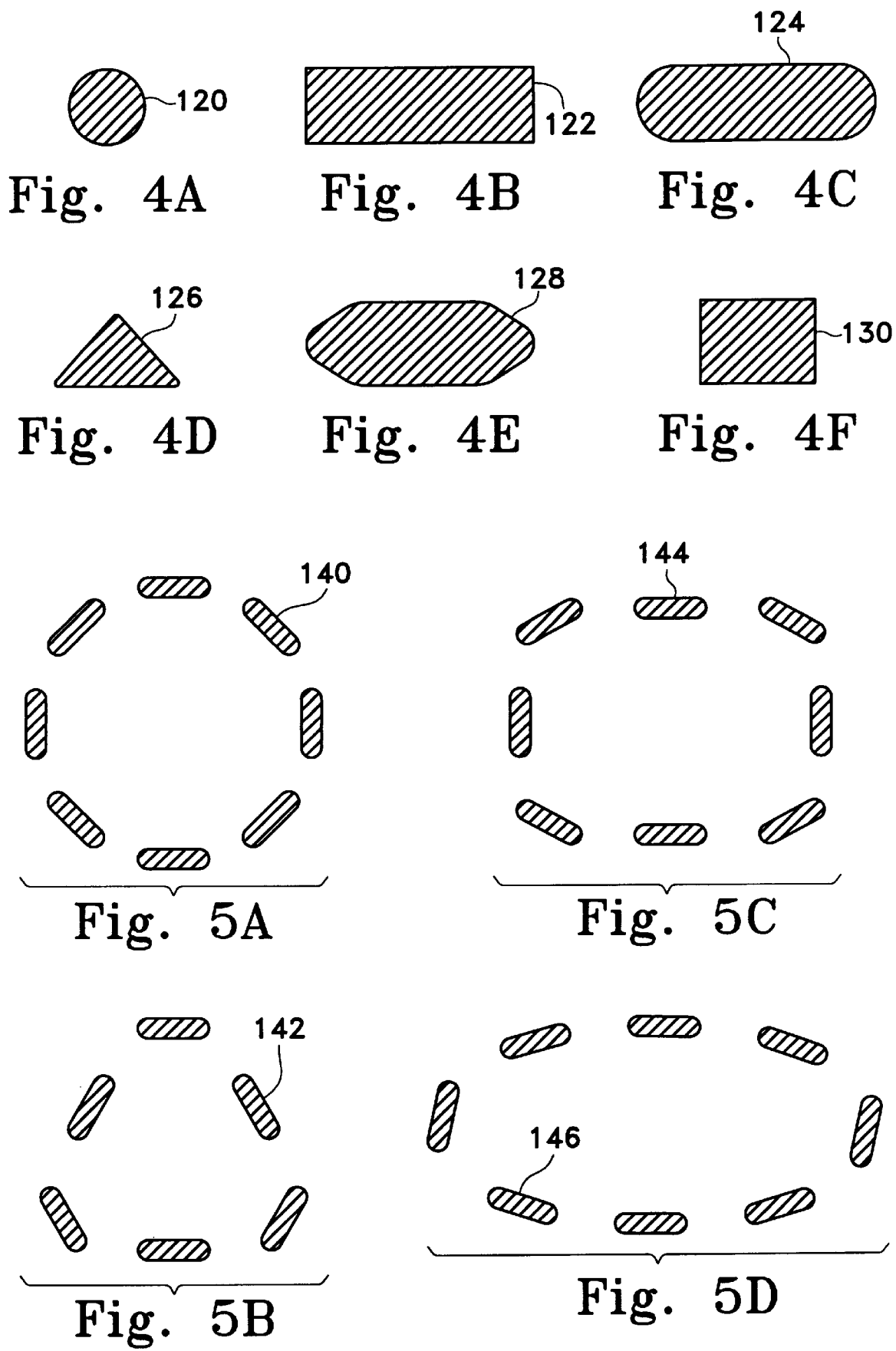

SUPER-ELASTIC ALLOY BRAID STRUCTURE

FIELD OF THE INVENTION

This invention is a stock structure. It is a braided tubular structure made up of a plurality of interwoven fibrous members, preferably ribbons, a majority of which comprise one or more superelastic and (at least) ternary alloys of nickel, titanium, and at least about 1.5% (wt) of one or more alloying members selected from the group consisting of vanadium, chromium, manganese, iron, and cobalt.

BACKGROUND OF THE INVENTION

There are a number of uses for superelastic alloy braids, particularly those which have small diameters of ¼ or less, which are also both flexible and consistent along their length in size and physical characteristics. I have found that braids made using nickel-titanium alloys, generically known as "nitinol" are not consistent in their physical properties or diameter. For instance, a braid made of a nickel-titanium alloy containing no more than trivial portions of iron or chromium does not retain its shape during subsequent handling or assembly steps even when heat-treated according to my invention. The diameter of such a braid varies as much as 10–20% causing the local stiffness to vary as well. I have surprisingly found that the use of a nickel-titanium alloy containing at least 1.5% (wt) of at least one alloying member selected from the group consisting of vanadium, chromium, manganese, iron, and cobalt solves these problems.

These braids are of special use in medical devices particularly when they are of smaller diameter. The invention is not so limited, however.

Other small diameter braids are known in the medical device area. For instance, there are a number of medical catheters discussed in the literature which have catheter bodies having multiply-wrapped reinforcing material. These catheters may include structures having braided bands or ones in which the spirally wound material is simply wound in one direction and the following layer or layers are wound in the other.

Crippendorf, U.S. Pat. No. 2,437,542, describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish-like layer. This latter material may be a tung oil base or a phenolic resin and a suitable plasticizer.

Similarly, U.S. Pat. No. 3,416,531, to Edwards, shows a catheter having braiding-edge walls. The device further has additional layers of other polymers such as TEFLON and the like. The strands found in the braiding in the walls appear to be threads having circular cross-sections.

U.S. Pat. No. 3,924,632, to Cook, shows a catheter body utilizing fiberglass bands wrapped spirally for the length of the catheter. As is shown in FIG. 2 and the explanation of the Figure at column 3, lines 12 and following, the catheter uses fiberglass bands which are braided, that is to say, bands which are spiralled in one direction cross over and under bands which are spiraled in the opposite direction. Additionally, it should be observed that FIG. 3 depicts a catheter shaft having both an inner lining or core 30 and an outer tube 35.

U.S. Pat. No. 4,425,919, to Alston, Jr. et al., shows a multilayered catheter assembly using multi-stranded flat wire braid. The braid 14 in FIG. 3 further covers an interior tubing or substrate 12.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is preferably made of an annealed copper wire which has been coated with a body-compatible polymer such as a polyurethane or a silicone. After coating, the copper wire is wound into a tube. The wound substrate is then coated with still another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is an aramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use with a guidewire.

U.S. Pat. No. 4,806,182, to Rydell et al, shows a device using a stainless steel braid imbedded in its wall and having an inner layer of a polyfluorocarbon. The process also described therein is a way to laminate the polyfluorocarbon to a polyurethane inner layer so as to prevent delamination.

U.S. Pat. No. 4,832,681, to Lenck, shows a method and apparatus useful for artificial fertilization. The device itself is a long portion of tubing which, depending upon its specific materials of construction, may be made somewhat stiffer by the addition of a spiral reinforcement comprising stainless steel wire.

U.S. Pat. No. 4,981,478, to Evard et al., discloses a multi-sectioned or composite vascular catheter. The interior section of the catheter appears to have three sections making up the shaft. The most interior (and distal) section, 47, appears to be a pair of coils 13 and 24 having a polymeric tubing member 21 placed within it. The next, more proximal, section is 41, and FIG. 4 shows it to be "wrapped or braided" about the next inner layer discussed just above. The drawing does not show it to be braided but, instead, a series of spirally wrapped individual strands. Finally, the outermost tubular section of this catheter core is another fiber layer 49, of similar construction to the middle section 26 discussed just above.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle.

U.S. Pat. No. 5,057,092, to Webster, Jr., shows a catheter device used to monitor cardiovascular electrical activity or to electrically stimulate the heart. The catheter uses braided helical members having a high modulus of elasticity, e.g., stainless steel. The braid is a fairly complicated, multi-component pattern shown very well in FIG. 2.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in.$^2$ or more. The flat strands themselves are said to have a width of between 0.006 and 0.020 inches and a thickness of 0.0015 and 0.004 inches.

Another variation which utilizes a catheter wall having helically placed liquid crystal fibrils is found in U.S. Pat. No. 5,248,305, to Zdrahala. The catheter body is extruded through an annular die, having relatively rotating inner and outer mandrel dies. In this way, the tube containing the liquid crystal polymer plastic-containing material exhibits a bit of circumferential orientation due to the rotating die parts. At column 2, line 40 and following, the patent suggests that the rotation rate of the inner and outer walls of the die may be varied as the tube is extruded, with the result that various sections of the extruded tube exhibit differing stiffnesses.

Japanese Kokai 05-220,225, owned by the Terumo Corporation, describes a catheter in which the torsional rigidity of the main body is varied by incorporating onto an inner tubular section 33, a wire layer which is tightly knitted at the proximal section of the catheter and more loosely knitted at a midsection.

None of the cited references specifies a tubular structure made of the materials specified in the invention.

SUMMARY OF THE INVENTION

This invention is a braided tubular structure made up of a plurality of interwoven fibrous members, a majority of which comprise one or more superelastic and (at least) ternary alloys of nickel, titanium, and at least about 1.5% (wt) of one or more alloying members selected from the group consisting of vanadium, chromium, manganese, iron, and cobalt. The braided structure may contain a minority of fibrous members of radio-opaque materials, polymeric materials, other metals or alloys, and highly conductive materials. Once the braid is woven, it preferably is heat treated to "set" the woven structure in its tubular form. The braid structure of this invention is particularly useful in applications where consistency of size (e.g., diameter) and physical properties (e.g., flexibility) is desirable. The cross section of the braid may be of circular, oval, radiused triangular, etc. shapes. Although ribbons are preferred as the filaments, wires and other such components are useful. This invention is especially suitable for use in medical such as catheter bodies and the like. In general, however, the inventive braids may be used to provide specific physical strengths of various types, e.g., torsional rigidity, stiffness, kink resistance, composite elasticity, etc. to a large number of different devices.

BRIEF DESCRIPTION OF THE DRAWINGS

FIGS. 4A–4F show cross-sectional views of a number of filaments suitable for use in the inventive braid.

FIGS. 5A–5D show various cross-sectional view of a number of structures made according to the invention.

DESCRIPTION OF THE INVENTION

This invention is a braided tubular structure made up of a plurality of interwoven fibrous members, a majority of which comprise one or more superelastic and (at least) ternary alloys of nickel, titanium, and at least about 1.5% (wt) of one or more alloying members selected from the group consisting of vanadium, chromium, manganese, iron, and cobalt. The braided structure may contain a minority of fibrous members of radio-opaque materials, polymeric materials, other metals or alloys, and highly conductive materials. Highly conductive materials are considered to be those having a specific resistance less than about 100 ohms per foot, preferably less than 50 ohms per foot, and most preferably less than about 10 ohms pre foot. Once the braid is woven, it preferably is heat treated to "set" the woven structure in its tubular form. The braid structure of this invention is particularly useful in applications where consistency of size (e.g., diameter) and physical properties (e.g., flexibility) is desirable. This invention is especially suitable for use in medical such as catheter bodies and the like. Because of the suppleness of the smaller sizes of the inventive braid, it may be used as electromagnetic shielding during various diagnostic procedures. In general, these inventive braids may be used to provide specific physical strengths of various types, e.g., torsional rigidity, stiffness, kink resistance, composite elasticity, etc. to a large number of different devices.

Figure 1:
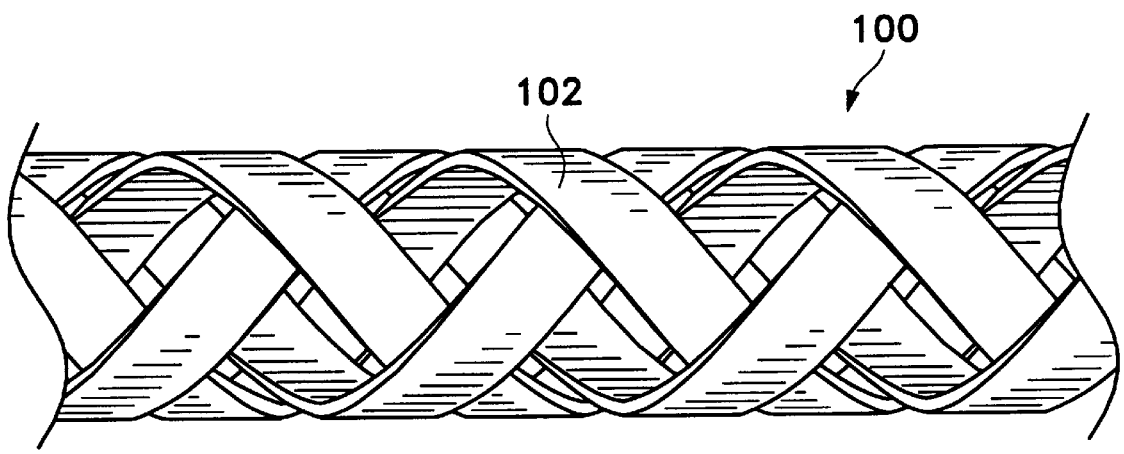
FIGS. 1 and 2 show a side view of sections of the inventive braid.

FIG. 1 shows one variation of the inventive metallic braid (100) made up of a number of metallic ribbons (102). A majority of the metallic ribbons (102) in braid (100) are superelastic alloys. In this variation, there is a significant amount of spacing between adjacent turns of the braid ribbons (102).

A technical basis for super-elastic alloys is found in the class of titanium/nickel materials known as nitinol—alloys discovered by the U.S. Navy Ordnance Laboratory. These materials are discussed at length in U.S. Pat. Nos. 3,174,851 to Buehler et al., 3,351,463 to Rozner et al., and 3,753,700 to Harrison et al. Alloys suitable for use in my invention are those which also containing at least 1.5% (wt) and up to about 8% (wt) or more, of one or more alloying members selected from the group consisting of vanadium, chromium, manganese, iron, and cobalt.

When using such superelastic alloys in my braids, an additional step may be desirable to preserve the shape of the braid. For instance, with a Cr-containing Ni/Ti superelastic alloy which has been rolled into a 1×4 mil ribbon and formed into a 16-member braid, some heat treatment is desirable. The braid may be placed onto a mandrel, usually metallic, of an appropriate size. The braid is then heated to a temperature of 650–750° F. for a few minutes, possibly (but not necessarily) annealing the constituent ribbon. After heat treatment, the braid retains its shape and the alloy retains its superelastic properties.

Metallic ribbons (102) that are suitable for use in this invention are desirably between 0.25 mil and 3.5 mil in thickness and 2.5 mil and 12.0 mil in width. By the term "ribbon", I intend to include elongated shapes, the cross-section of which are not square or round and may typically be rectangular, oval or semi-oval. They should have an aspect ratio of at least 0.5 (thickness/width).

The ribbons (102) making up the braid (100) shown in FIG. 1 may also contain a minor amount of non-superelastic materials. Although metallic ribbons may be preferred as the ancillary materials because of their strength-to-weight ratios, fibrous materials (both synthetic and natural) may also be used. Preferred, because of cost, strength, and ready availability are stainless steels (SS304, SS306, SS308, SS316, SS318, etc.) and tungsten alloys. In certain applications, where radioopacity is desired, radiopaque metals and alloys, e.g., gold, platinum, palladium, rhodium, rhenium, tungsten, their alloys and mixtures, etc. may be used. A platinum alloy with a few percent of tungsten is preferred partially because of its radiopacity.

Suitable non-metallic ribbons include high performance materials such as those made of polyaramids (e.g., KEVLAR) and carbon fibers.

The braids of this invention may be made using commercially available tubular braiders. The term "braid" is meant to include tubular constructions in which the fibrous materials making up the construction are woven in an in-and-out fashion as they cross to form a tubular member defining a single passageway. The braids may be made up of a suitable number of ribbons, typically six or more. Ease of production on a commercial braider typically results in braids having eight or sixteen ribbons.

The braided structure shown in FIG. 1 has a nominal pitch angle of 45°. Clearly the invention is not so limited. Other braid angles from 20° to 60° are also suitable. An important variation of this invention is the ability to vary controllably the pitch angle of the braid either at the time the braid is woven or at the time the braid is assembled into another device.

Although the braid (100) shown in FIG. 1 and the other Figures has a single size of ribbon, the braid need not be so limited; multiple sizes of ribbon may be used as desired. The major limitations are simply the size, e.g., diameter, of the overall braid as finally constructed and the desired added stiffness to be added to the braid structure.

The braids typically useful in this invention comprise an even number of ribbons: one half of the ribbons wound one way, i.e., clockwise, and the remainder are wound the other way. A typical braid will be of eight to 16 ribbons. The braid may have a single pitch, an angle of a constituent ribbon measured against the axis of the braid, or it may have a pitch which varies along the axis of the braid.

The braid structure (100) shown in FIG. 1 has a relatively constant diameter. Although the heat treatment step noted above in conjunction with the specified alloys results in a tubular structure having a shape corresponding to the particular mandrel chosen for the heat treating step, the shape of the mandrel and hence the shape of the tubular structure may have a varying, e.g., an increasing or decreasing diameter.

The braid structure (100) may be rough to the touch if not covered or further processed. Procedures such as rolling, sanding, or grinding may be used to smooth the surface of the braid structure if so desired. Removal of any produced particulates is, of course, desirable.

Figure 2:
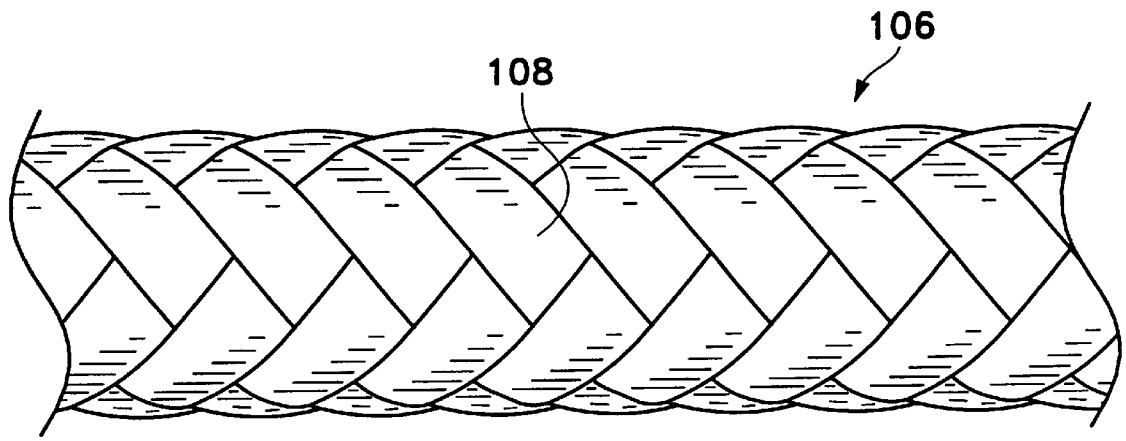

FIG. 2 shows a variation of the inventive braid structure (106) in which the spacing between the adjacent ribbons (108) is minimal. That is to say that each ribbon (108) is adjacent the next. This tight structure is typically stiffer than more loosely woven braids.

Figure 3:
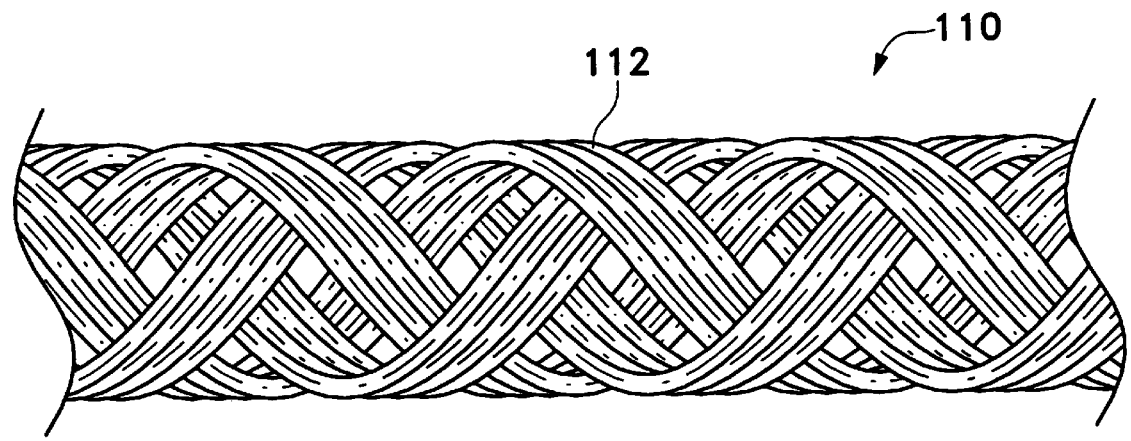
FIG. 3 shows a side view of a section of the inventive braid having multiple members in the braiding fabric.

FIG. 3 shows a close-up of another variation (110) of the inventive device in which the filamentary members (112) are not a single weave as is shown in the Figures above. The filamentary members (112) weave around the tubular structure (110) in a band of (for instance) four to five filaments much in the same way that the single ribbon is woven around the FIGS. 1 and 2 devices. I refer to this variation as a "multiple member braid structure."

FIGS. 4A–F depict, in cross section, a number of filamentary profiles suitable for use in this invention. The round cross-section (120 in FIG. 4A) is a wire. The rectangular cross-section (122 in FIG. 4B) has a wide axis and a narrow axis. The broad axis should be no larger than 12 mils for most endovascular catheter applications but may be larger for other uses, e.g., as a stent or endoscope component. The oval cross-section (124 in FIG. 4C) may be used in place of the rectangular cross-section as desired. Cross-section (126 in FIG. 4D) is triangular. Cross-section (128 in FIG. 4E) is polygonal, specifically hexagonal. Cross-section (130 in FIG. 4F) is square.

Finally, this invention is not limited to a tubular structure which is simply round (140) as is shown in FIG. 5A. Other cross-sections contemplated in this invention include triangular (e.g., radiused triangular) (142) as is shown in FIG. 5B and radiused square or rectangular (144) as is shown in FIG. 5C. An oval shape (146) is shown in FIG. 5D.

This invention has been described and specific examples of the invention have portrayed. The use of those specifics is not intended to limit the invention in any way. Additionally, to the extent that there are variations of the invention which are within the spirit of the disclosure and yet are equivalent to the inventions found in the claims, it is my intent that those claims cover those variations as well.

I claim as my invention:

1. A tubular structure comprising a plurality of constituent filaments:
    wherein said plurality of constituent filaments are interwoven into a braid forming an inner passageway,
    wherein at least some of said constituent filaments are superelastic alloy constituent filaments,
    wherein said superelastic alloy constituent filaments have a cross section with a maximum dimension no greater than about 12.0 mils, and
    wherein said superelastic alloy comprises a nickel titanium alloy containing at least about 1.5%(wt) of at least one alloying element selected from the group consisting of vanadium, chromium, manganese, iron, and cobalt.

2. The tubular structure of claim 1 wherein the constituent filaments have cross-sections selected from rectangular, circular, oval, square, and triangular.

3. The tubular structure of claim 1 wherein the constituent filaments comprise ribbons having a rectangular cross-section.

4. The tubular structure of claim 3 wherein the ribbon rectangular cross section have a major axis between 2.5 and 12.0 mils and a minor axis between 0.25 and 3.0 mils.

5. The tubular structure of claim 1 wherein the tubular structure has been heat-treated after braiding to impart a consistent diameter to said structure.

6. The tubular structure of claim 1 wherein a minority of said constituent filaments comprises conductor filaments interwoven into said braid, said conductor filaments having a specific resistance of less than about 100 ohms per foot.

7. The tubular structure of claim 1 wherein a minority of said constituent filaments comprises radio-opaque filaments interwoven into said braid, said radio-opaque filaments comprising at least one member selected from the group consisting of platinum, palladium, rhodium, rhenium, ruthenium, gold, tungsten, their mixtures and alloys.

8. The tubular structure of claim 1 wherein a minority of said constituent filaments comprises polymeric filaments interwoven into said braid.

9. The tubular structure of claim 1 wherein the tubular structure is interwoven using a single member braid structure.

10. The tubular structure of claim 1 wherein the tubular structure is interwoven using a multiple member braid structure.

11. The tubular structure of claim 1 wherein the tubular structure has a cross section selected from circular, oval, triangular, rectangular, and square.

12. The tubular structure of claim 1 wherein at least a portion of the filaments have a cross section selected from circular, oval, triangular, rectangular, and square.

13. The tubular structure of claim 1 wherein said at least one alloying element selected from the group consisting of chromium and iron.

14. The tubular structure of claim 1 wherein said at least one alloying element is chromium.

15. A tubular structure comprising a plurality of constituent ribbons:

wherein said plurality of constituent ribbons are interwoven into a braid forming an inner passageway, wherein at least some of said constituent ribbons are superelastic alloy constituent rectangular cross-section ribbons, wherein said superelastic alloy constituent ribbons having a cross section having a major axis between 2.5 and 12.0 mils and a minor axis between 0.25 and 3.0 mils, and wherein said superelastic alloy comprises a nickel-titanium alloy containing at least about 1.5% (wt) of at least one alloying element selected from the group consisting of vanadium, chromium, manganese, iron, and cobalt.

16. The tubular structure of claim 15 wherein the tubular structure has been heat-treated after braiding to impart a consistent diameter to said structure.

* * * * *